United States Patent [19]

Lambert

[11] Patent Number: 4,863,052
[45] Date of Patent: Sep. 5, 1989

[54] DISPOSABLE CONTAMINATED MATERIAL CONTAINER

[75] Inventor: William E. Lambert, Richmond, Va.

[73] Assignee: Union Camp Corporation, Wayne, N.J.

[21] Appl. No.: 214,719

[22] Filed: Jun. 5, 1988

[51] Int. Cl.⁴ .............................................. B65D 5/46
[52] U.S. Cl. ..................... 220/1 T; 206/438; 206/366; 229/907; 229/117.14
[58] Field of Search ............... 220/1 T, 402, 403; 206/438, 366; 229/52 B, 907, 11

[56] References Cited

U.S. PATENT DOCUMENTS

| | | | |
|---|---|---|---|
| 2,730,294 | 12/1952 | Stavis | 229/52 B |
| 2,971,688 | 3/1957 | Akers | 229/907 |
| 3,940,055 | 2/1976 | Rowley | 229/52 B |
| 4,003,515 | 1/1977 | Steele | 229/52 B |
| 4,315,592 | 2/1982 | Smith | 206/366 |
| 4,534,489 | 8/1985 | Bartlett | 220/1 T |
| 4,674,676 | 6/1987 | Sandel | 229/907 |

Primary Examiner—George E. Lowrance
Assistant Examiner—Gilbert W. Reece
Attorney, Agent, or Firm—Edward J. Sites

[57] ABSTRACT

Portable containers suitable for use as disposable contaminated material containers are provided. The containers include a top closure including first and second closure flaps whereby the first closure flap has a central opening for filling the box and a handle member for holding it. The handle member can be inserted into a corresponding aperture of the second closure flap which protects the handle from being contaminated during use. The design also includes using an interior space defined by an internal open-ended container wrapped in a preferred thermoplastic bag. This feature enables the container to resist leakage of contaminated materials and the risk of puncture of the container by sharp objects.

17 Claims, 3 Drawing Sheets

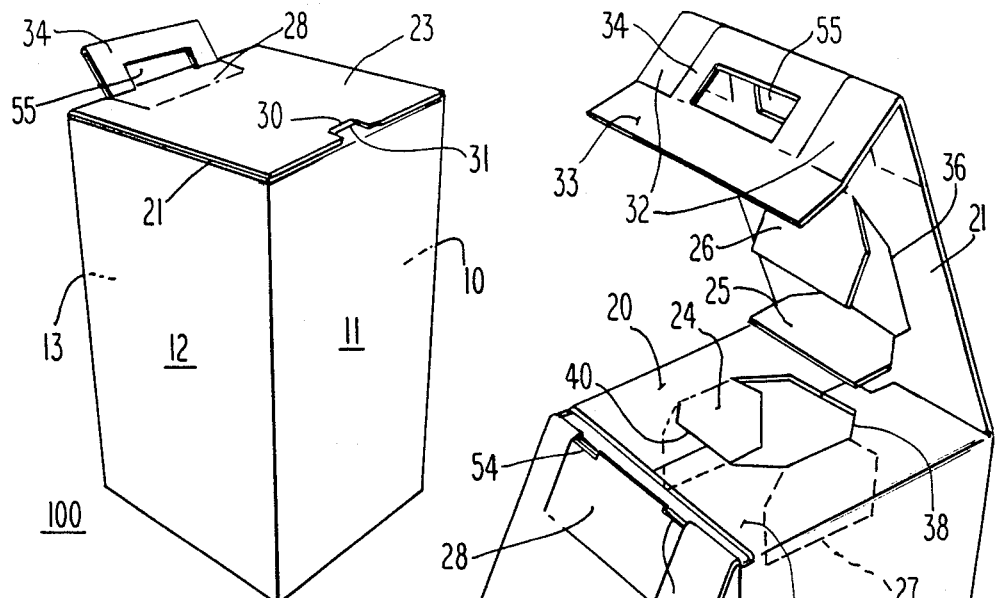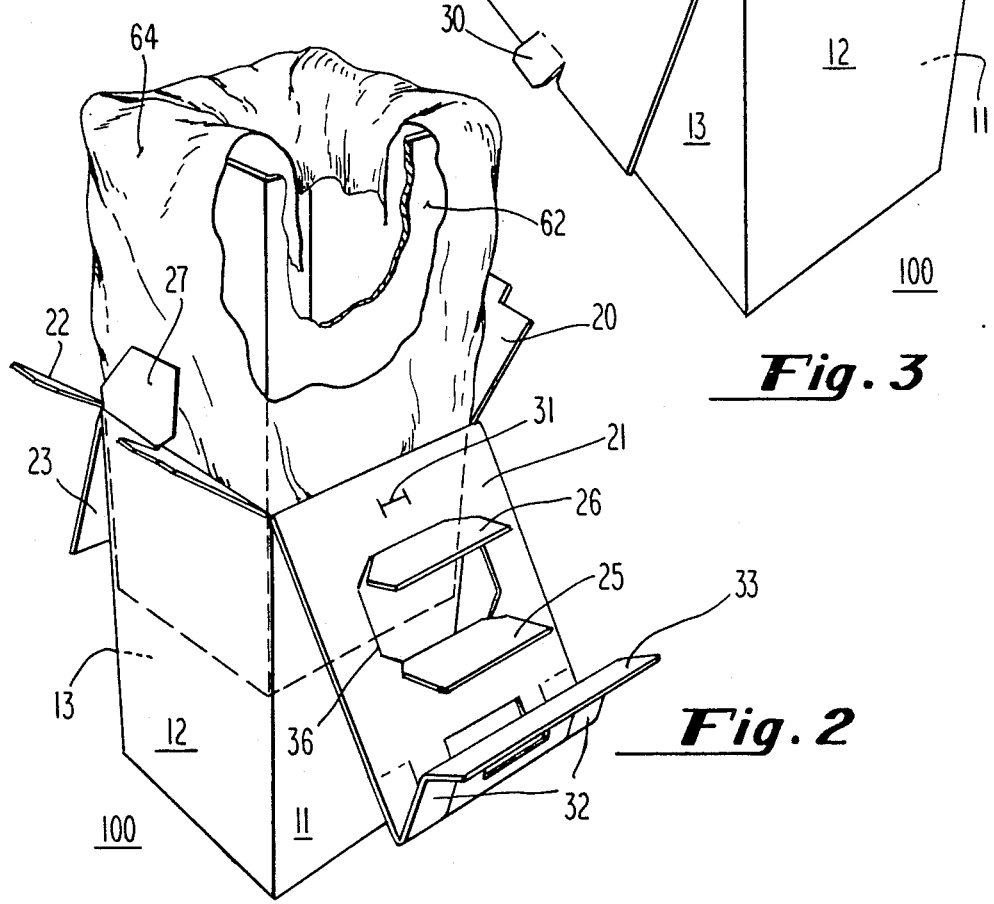

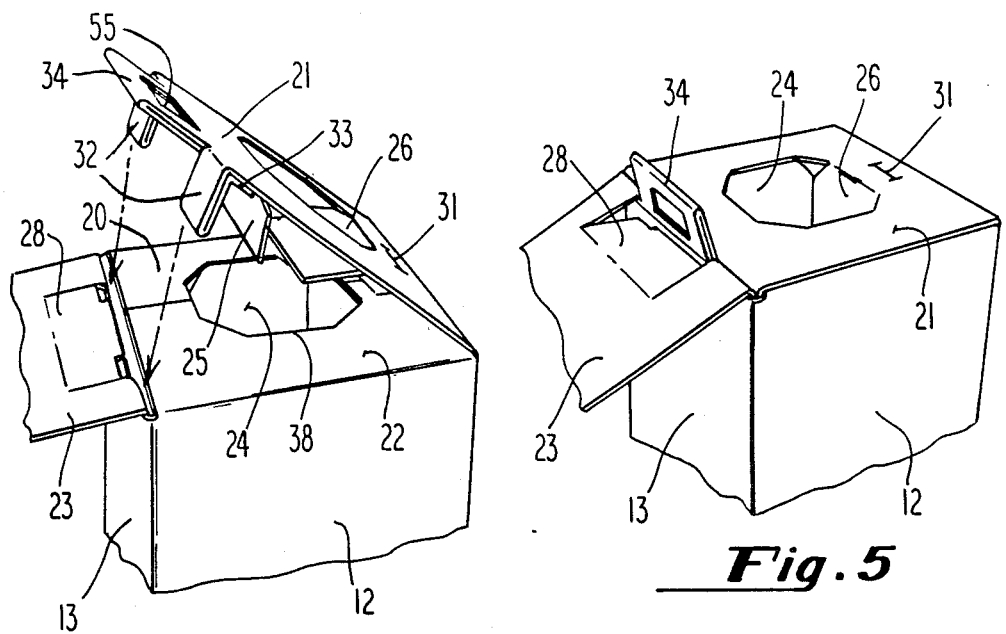
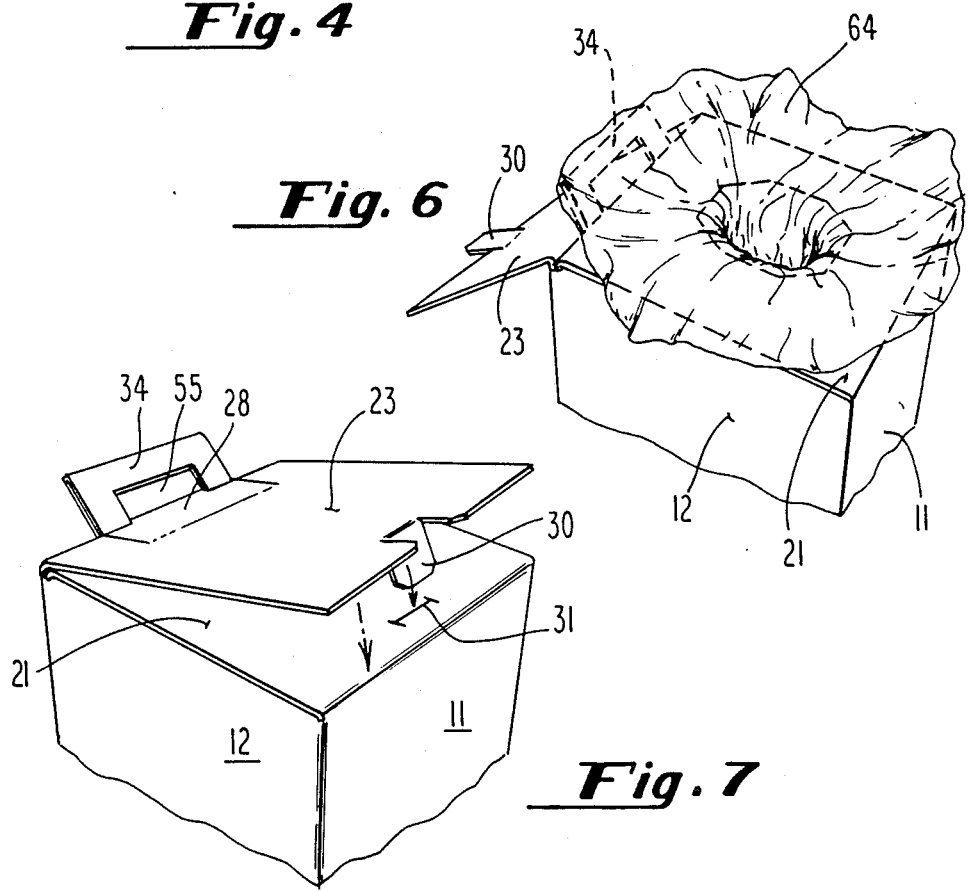

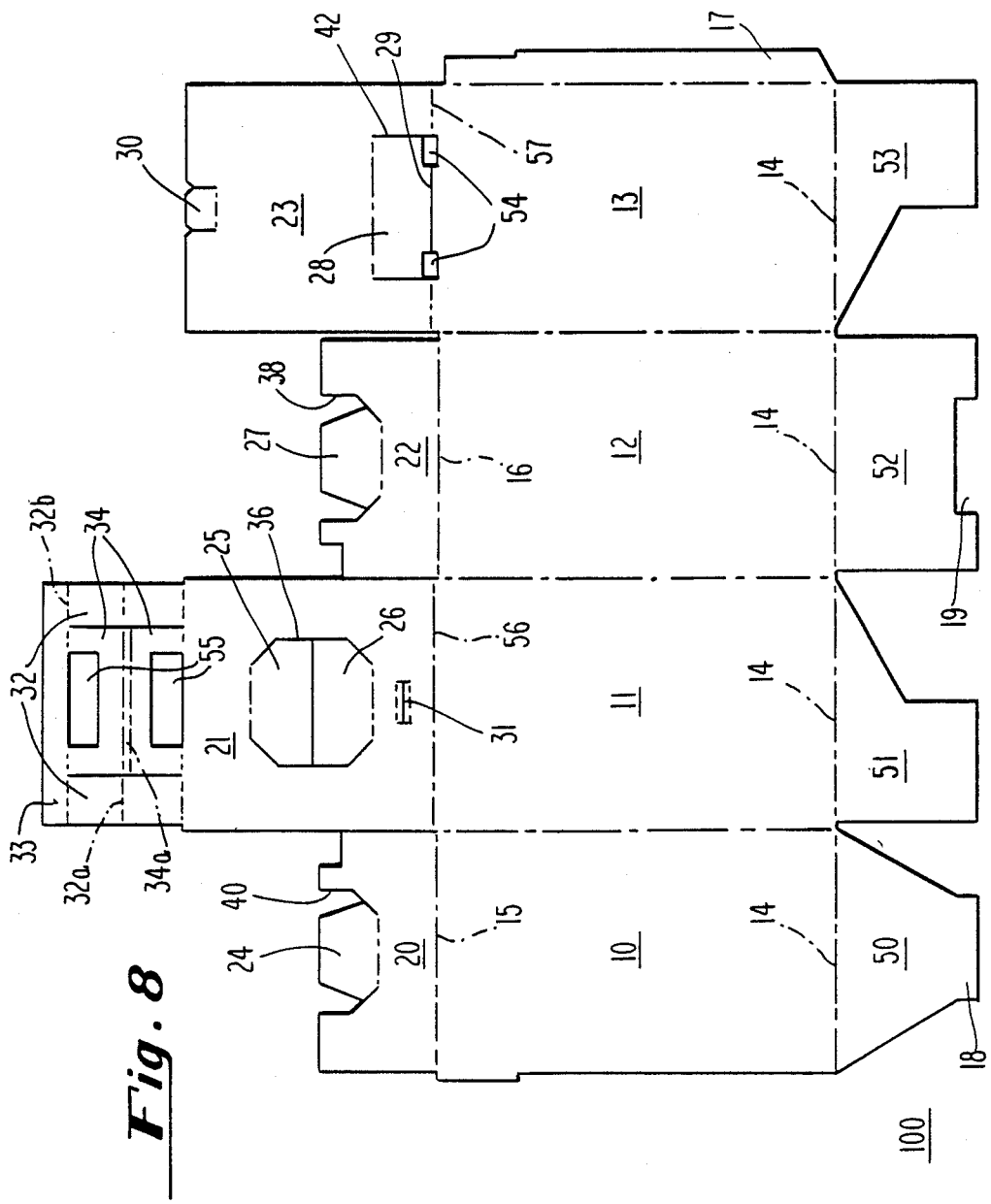

DISPOSABLE CONTAMINATED MATERIAL CONTAINER

FIELD OF THE INVENTION

This invention relates to containers used in hospital environments, especially those suitable for the collection of contaminated materials, such as dressings, body tissues, hypodermic needles and other waste.

BACKGROUND OF THE INVENTION

The health care community is particularly sensitive to the collection and disposal of waste materials in hospitals in the wake of recent and growing concern regarding infectious diseases, such as hepatitis and AIDS. It is now more important than ever that contaminated materials remain sealed or secured so as to not cause persons handling them to become infected. Containers used for holding such waste are presently incinerated for health and safety reasons and generally are constructed of cardboard or light plastics. However, since these containers often hold "sharps", e.g., hypodermic needles and other pointed objects, leaking body fluids, in combination with a threat of puncturing the skin of hospital workers, are serious problems.

One prior art method of waste disposal often employed by hospitals is to use "red" bags. Such bags generally comprise polyethylene which is dyed red in color and inserted into a stainless steel can. Contaminated materials, including hypodermic needles and the like, are then inserted into the red bag. When the bag is full, it is usually removed by hospital workers and carried to the incinerator. Since the bag is easily punctured by sharp implements, hospital workers are at serious risk of injury and disease.

One modern attempt at solving this problem is to use corrugated boxes having a polyethylene liner. These boxes enable contaminated material to be inserted into the polyethylene bag within the box. When full, both the box and the polyethylene bag are carried to an incinerator for disposal. While the corrugated box gives substantial additional protection to the bag for preventing the penetration of sharps, there are several shortcomings. One difficulty associated with using the corrugated box method, is that hospital workers often come into imminent contact with the box during handling. Since the outside of the box often is sometimes contaminated by leakage and spillage of body fluids, this contact presents a hazard. While it has been suggested that holes could be punched in the sides of these cartons for handling by hospital workers, this would require that the fingers of the workers be inserted into the box, again exposed to contaminated material and sharps. It has also been suggested to attach a separate grip to the side of the box for safer handling. However, this attempted solution is understood to weaken the box, and generate local stress points for tearing of the corrugated material. The consequences of a torn handle and a box spilled of its contents makes this solution highly undesirable. A further attempt at this problem has been to provide a false bottom to the boxes so that sharps thrown directly into the box can not easily puncture the bottom. Such a construction has presented several problems, however. The boxes are understood to be more difficult to assemble from their knockdown condition. Additionally, the volume of the box is generally less than it would be without a false bottom.

Accordingly, a safer method of disposing and incinerating hospital waste is needed. There is also a need for a contaminated material container having a strong handle for carrying up to about 100 lbs. of contaminated waste. This handle should be protected from contamination during use and should enable a worker to readily pick up the box without having to contact the remainder of the outside surface of the box.

SUMMARY OF THE INVENTION

Portable containers, suitable for use as disposable contaminated material boxes, are provided by this invention. The portable container includes a top closure having first and second closure flaps secured to a pair of oppositely facing side panels of the container along a hinge line. The first closure flap includes a central opening for receiving material, such as hospital waste during use. The first closure flap also includes a handle member disposed on an edge opposite its hinge line. This handle is designed to be inserted into a corresponding aperture of the second closure flap during and after filling of the container. When the container is being loaded with material, the handle can be covered by inserting it through the aperture of the second closure flap, thereby protecting it from contamination.

Accordingly, the portable container, including the integral handle described herein, enables hospital workers to carry the full boxes without having to come into direct contact with contaminated materials and sharps, which may have punctured or otherwise penetrated the box. Additionally, the handle is designed to be strong to enable the box to be carried easily without tearing or spilling the container's contents.

In the preferred embodiments of this invention, the handle can be further protected by a hinged flap portion, of the second closure flap, which is disposed over the aperture after the handle is inserted. There can also be an internal open-ended container wrapped with a plastic liner within the preferred box embodiment. In the latter embodiment, the double-box-thickness, preferably containing corrugated material, is suitably designed to reduce the risk of penetration by sharps and drastically reduce the problems of leakage. It is further noted that this open-ended container can be designed to fit with the liner to fit snugly within the portable outer container for better volumetric efficiency.

It is therefore an object of this invention to provide portable containers having integral handles for enabling the transport of the container without risk of damage to its structure.

It is also an object of this invention to provide portable waste disposal systems suitable for use as contaminated material containers which reduce the risk of injuring hospital workers.

It is a further object of this invention to provide an contaminated material container that includes an integral handle that remains sanitary.

With these and other objects in view, this invention resides in the novel construction, combination, arrangement of parts and methods substantially described and more particularly defined in the attached claims.

BRIEF DESCRIPTION OF THE DRAWINGS

The accompanying drawings illustrate a complete embodiment of the invention according to a preferred embodiment for a practical application of the principles thereof and in which:

FIG. 1: is a perspective view of a preferred container embodiment with all of its closures and locking tabs in position to complete the closure prior to handling;

FIG. 2: is an exploded perspective view of the container of FIG. 1, illustrating how a preferred open-ended container and plastic liner can be inserted into the preferred portable container, and further illustrating a peel-back view of the open-ended container under the plastic liner;

FIG. 3: is a perspective view of the preferred container of FIG. 1 illustrating a preferred top closure flap construction including an integral handle prior to securing the flap;

FIG. 4: is a perspective view of the preferred container prior to inserting biasing tabs of the flap of FIG. 3 into the container;

FIG. 5: is a perspective view of the preferred container after the biasing tabs of FIG. 4 are inserted against an inner surface of the container;

FIG. 6: is a perspective view of the preferred container after an extended portion of the liner has been pulled through the central opening of one of the top closure flaps prior to filling;

FIG. 7: is a perspective view of the preferred container after the handle member is inserted through an aperture of a second top closure flap and prior to engaging the locking tab; and FIG. 8: is a planar view of a blank of the preferred container of the present invention.

DESCRIPTION OF THE INVENTION

This invention provides a portable container having a bottom closure and side panels which further comprises a top closure having first and second closure flaps secured to opposite side panels of the container along a hinge line so that the flaps can be folded into over-lapping horizontal positions to close the container. The first closure flap of the top closure includes a central opening therein and a handle member disposed on an edge of the first closure flap opposite its hinge line. The second closure flap comprises an aperture disposed to receive the handle member of the first closure flap.

In more preferred embodiments of this invention, the handle member comprises a two-ply, folded extension of the first closure flap. The handle member also preferably includes a biasing tab or tabs disposed to lie flat against an inner surface of the side panel connected to the second closure flap when the first closure flap is in a horizontal position. The biasing tab may conform to any particular shape, however, two-ply, folded extensions of the first closure flap are preferred.

The portable container further preferably includes a hinged flap portion, or a separately attached flexible cover, extending from the second closure flap and disposed to cover a portion of the aperture of the second flap after the handle member is inserted therethrough. This feature is important for keeping the handle sanitary during the filling of the container, for example, when contaminated waste is inserted. The hinged flap portion or flexible cover of the second closure flap ideally comprises an extended tab portion for inserting under the handle member to generally provide a better fit.

The more preferred second closure flap of this invention also comprises a locking tab disposed on a non-hinged edge for securing the second closure flap prior to handling and disposal. The first closure flap, in this regard, preferably includes a slot for receiving this locking tab.

In further embodiments of this invention, the first closure flap comprises a folding flap portion disposed to cover a portion of its central opening. The folding flap portion can conveniently be manufactured in the blank of the box and provides a "funnel-type" channel for objects thrown into the container. This feature directs sharps toward the bottom of the box and further reduces the risk of side puncture. Also included in more preferred embodiments are third and fourth closure flaps disposed on a remaining two of the four side panels which can be folded in conjunction with the first two closure flaps to form a top closure. The third and fourth closure flaps preferably include cut-out portions which generally correspond to the central opening of the first closure flap when the first, third and fourth closure flaps are disposed into over-lapping horizontal positions.

Referring now to the interior of the preferred containers, additional safety features will now be described. The preferred containers of this invention include a thin sheet of flexible material, preferably a thermoplastic bag, and more preferably a polyethylene bag, disposed to cover an inner surface of the container. In an important aspect of this invention, an openended container, preferably comprising a bottom and four side panels, is disposed within the thermoplastic bag to further reduce the incidence of puncture and leakage. Ideally, the opened-ended container is disposed with the thermoplastic bag to snugly fit into the inner cavity of the portable container. This "box within a box" design permits full use of the volume of the portable container and, accordingly, increases the volumetric efficiency of the box. It is understood that the prior art contaminated material containers often did not use their full capacity because of binding of the polyethylene liner. The preferred thermoplastic bag of this design includes an extended open portion for disposing through the central opening of the first closure flap, whereby materials, such as contaminated material, can be disposed within the open-ended container through the extended open portion of the thermoplastic bag.

Referring now to the drawings, and particularly to FIG. 8 thereof, a blank of the preferred box design will now be fully described. The portable container 100, manufactured from this blank, includes a bottom closure consisting of bottom flaps 50, 51, 52 and 53 and four side panels 10, 11, 12 and 13. The container 100 further comprises a top closure comprising first and second closure flaps 21 and 23 respectively. These flaps 21 and 23 are secured to opposite side panels 11 and 13 of the container along respective hinge lines 56 and 57 so that the flaps 21 and 23 can be folded into over-lapping horizontal positions to close the container 100. The first closure flap 21 comprises a central opening 36 therein and a handle member 34 disposed on a side of the first closure flap 21 opposite its hinge line 56. The handle member 34, preferably is provided by two generally rectangular cut-outs 55 in the blank. The second closure flap 23 comprises an aperture 42 disposed to receive the handle member 34.

The portable container formed from the blank of FIG. 8, can be made of any flexible sheet of material, such as corrugated board, fiberboard, or the like of a weight suitable for the type of carton to be constructed. Preferably the material can be incinerated for sanitary disposal of contaminated material. The blank illustrated in FIG. 8 will form a container which is generally rectangular in side view, comprising about a square crosssection. It is understood that such a container can be square, tall, medium or other shape, in which case, the shape of the blank will be modified accordingly.

Construction of a preferred container from the blank of FIG. 8 will now be addressed. The bottom flaps are attached to the side panels 10, 11, 12, and 13 along a longitudinal score line 14. The side panels 20, 21, 22 and 23 are attached along score lines 15, 16, 56 and 57 respectively. In setting up the blank into a box, the outer edges of the side panels 10 and 13 are preferably joined together and secured with tab 17 and adhesive. It is understood that various other forms of attachment can be used, such as tape or staples, as those familiar to this art are aware.

The bottom closure of this invention will now be described. In the preferred construction, it is noted that flap 52 can be folded inwardly and that flaps 51 and 53 can be folded over flap 52, prior to folding over flap 50 and securing tab 18 into slot 19 to form the bottom of the container 100.

Referring now to FIGS. 1-7, the construction and use for the top closure will now be described. Flaps 20 and 22 are provided with cutout portions 38 and 40 which correspond to a central opening 36 in flap 21. These flaps 20 and 22 further include folding flap portions 24 and 27. The closure flaps 20 and 22, herein referred to as the third and fourth closure flaps, are folded inwardly to a horizontal position, while their folding flap portions 24 and 27 are further bent to approximately a vertical position within the container 100. The first closure flap 21 is then folded onto flaps 20 and 22 so that its central opening 26 overlies the opening formed by cutout portions 40 and 38. Flap 21 also includes folding flap portions 25 and 26 which can be vertically disposed within the container 100 to form a funnel-type opening with folding flap portions 24 and 27, as described further in FIG. 5. The preferred polyethylene liner 64 can then be pulled through the opening for filling the preferred internal, open-ended container 62 as described in FIGS. 2 and 6.

Referring now to FIGS. 3-5, the assembly of the handle member 34 will now be described. The preferred handle member comprises handle 34 which is folded downwardly about score line 34a. Biasing tabs 32 are also folded downwardly about score line 32a. This embodiment further provides a biasing flap 33, for adding additional support to the handle structure during use. The biasing flap 33 is preferably folded upwardly along score line 32b. The preferred folding arrangement is further described in more detail by FIG. 3. After folding the handle member 34, biasing tabs 32 and biasing flap 33 about their respective score lines, the assembly is compressed as described in FIG. 4 so that the biasing tabs 32 can be disposed to lie flat against an inner surface of the side panel 13 connected to the second closure flap 23 when the first closure flap 21 is in a horizontal position. Simultaneously, the biasing flap 33 is disposed and secured between closure flaps 21 and the combination flaps 20 and 22. The inserted first closure flap 21 is fully illustrated in FIG. 5.

Prior to use, it is desirable that the handle member 34 be inserted through aperture 42 and secured by hinge flap portion 28 and extended tab portion 29. The hinge flap portion 28 of the second closure flap 23 includes two cutouts 54 for enabling the handle member 34 to have a flexible degree of rotation once the container 100 is fully assembled for disposal. The hinge flap portion is an important feature of this invention, since it protects the handle member 34 during the filling of the container 100 from contaminated waste. Thus, a sanitary handle may be gripped by a hospital worker upon disposal, such as that described in FIG. 7.

Referring now to the constructions of FIGS. 1 and 7, the locking mechanism will now be described. Upon filling the container 100, the second closure flap 23 can be folded into a horizontal position to seal the central opening 36 and any contaminated liner portion present on the outside of the box, if any. The locking mechanism consists of locking tab 30 and receiving slot 31 which can be engaged to secure the second closure flap in a horizontal position. The final preferred construction of the box prior to disposal is illustrated in FIG. 1.

From the foregoing it can be realized that this invention provides a safer method of disposing and incinerating hospital waste. Portable containers have been described which include a strong handle protected from contamination during the use of the container. Accordingly, the containers described enable hospital workers to carry boxes filled to their capacity without having to come into direct contact with the contaminated materials and/or sharps. Although various embodiments have been illustrated, this was for the purpose of describing, but not limiting, the invention. Various modifications, which will become apparent to one skilled in the art, are within the scope of this invention described in the attached claims.

What is claimed is:

1. A portable container having a bottom closure and side panels, comprising:
   a top closure comprising first and second closure flaps secured to opposite side panels of said container along respective hinge lines so that said flaps can be folded into over-lapping horizontal positions to close the container;
   said first closure flap comprising a central opening therein and a handle member comprising a two-ply, folded extension of said first closure flap disposed on an edge of said first closure flap opposite its hinge line;
   said handle member further comprising a biasing tab comprising a two-ply, folded extension of said first closure flap disposed to lie against an inner surface of the side panel connected to said second closure flap when said first closure flap is in a horizontal position;
   said second closure flap comprising an aperture disposed to receive said handle member.

2. A portable container having a bottom closure and four side panels comprising:
   a top closure comprising first and second closure flaps secured to opposite side panels of said container along respective hinge lines so that said flaps can be folded into over-lapping horizontal positions to close the container;
   said first closure flap comprising a central opening therein and a handle member disposed on a side of said first closure flap opposite its hinge line; and
   said second closure flap comprising an aperture disposed to receive said handle member and a hinged flap portion disposed to cover a portion of said aperture after said handle member is inserted therethrough.

3. The portable container of claim 2 wherein said hinged flap portion comprises an extended tab portion for inserting under said handle member.

4. The portable container of claim 3 wherein second closure flap comprises a locking tab disposed on a non-hinged edge of said second closure flap.

5. The portable container of claim 4 wherein said first closure flap comprises a slot for receiving said locking tab of said second closure flap.

6. The portable container of claim 5 wherein said first closure flap comprises a folding flap portion disposed to cover a portion of said central opening.

7. The portable container of claim 2 further comprising third and fourth closure flaps disposed on a remaining two of said four side panels.

8. The portable container of claim 7 wherein said third and fourth closure flaps comprise cutout portions which correspond to said central opening of said first closure flap when said first, third and fourth closure flaps are disposed into overlapping horizontal positions.

9. The portable container of claim 2 wherein said container further comprises a thin sheet of flexible material disposed to cover an inner surface of said container.

10. The portable container of claim 9 wherein said thin sheet of flexible material comprises a thermoplastic bag.

11. The portable container of claim 10 wherein said thermoplastic bag comprises polyethylene.

12. The portable container of claim 10 further comprising an open-ended container disposed within said thermoplastic bag.

13. The portable container of claim 12 wherein said openended container comprises a bottom and four side panels.

14. The portable container of claim 13 wherein said openended container is disposed with said thermoplastic bag to snugly fit into an inner cavity of said portable container.

15. The portable container of claim 14 wherein said thermoplastic bag comprises an extended open portion for disposing through said central opening of said first closure flap.

16. The portable container of claim 15 wherein said contaminated material is disposed within said open-ended container.

17. A portable contaminated material container formed from a one-sheet blank having a bottom closure and four side panels, comprising:
   a top closure comprising four closure flaps secured to each side panel along a hinge line so that the four closure flaps can be folded into overlapping horizontal positions to close the container;
   a first flap of said closure flaps comprising a central opening in open communication with an inner cavity of said container and further comprising a handle portion disposed on a side of said first closure flap opposite its hinge line;
   a second flap of said closure flaps disposed opposite said first flap and comprising an aperture disposed to receive said handle portion of said first flap whereby said second flap is disposed to lie over substantially all of an exposed side of said handle portion and protect said exposed side of said handle portion from said contaminated material during filling of said container.

* * * * *